United States Patent [19]
Blacklock

[11] Patent Number: 5,653,151
[45] Date of Patent: Aug. 5, 1997

[54] REVERSIBLE RATCHET DRIVING TOOL

[76] Inventor: Gordon D. Blacklock, 14116 Grand NE., Albequerque, N. Mex. 87123

[21] Appl. No.: 427,256

[22] Filed: Apr. 24, 1995

[51] Int. Cl.$^6$ .................................................. B25B 13/46
[52] U.S. Cl. .............................. 81/60; 81/58.5; 81/438
[58] Field of Search ........................ 81/58.5, 60, 438, 81/439

[56] References Cited

U.S. PATENT DOCUMENTS

| | | | |
|---|---|---|---|
| 161,022 | 3/1875 | Freeman | 81/58.5 |
| 4,056,020 | 11/1977 | Coviello | 81/438 |
| 4,273,173 | 6/1981 | Smith et al. | 81/438 |
| 4,808,106 | 2/1989 | Foreman | 81/60 |

FOREIGN PATENT DOCUMENTS

| 670225 | 2/1929 | France | 81/58.5 |
|---|---|---|---|

*Primary Examiner*—James G. Smith
*Attorney, Agent, or Firm*—Terrance L. Siemens

[57] ABSTRACT

A two sided ratcheting driving tool. Each side has a rotatable receptacle constrained to rotate in only one direction by interengaging teeth formed in the receptacle and in its housing. A leaf spring urges the receptacle into the engaged position with respect to the housing. In one direction, the receptacle is locked to the housing, and thus drives a tool such as a screw driver blade or a socket. In the other direction, torque causes the receptacle to overcome the spring and disengage from the housing. Thus, conventional, intermittent one way rotation is assured. The receptacle has a square hole formed therein, for receiving a tool. The tool comprises a square block cooperating with the square hole of the receptacle, and has two oppositely oriented blades, sockets, or other tools. Direction of operation is reversed by using a different one of the oppositely oriented tools. No adjustment of a lever is required. The novel wrench is unencumbered by complicated internal parts, but still often reversibility and interchangeability of tools.

16 Claims, 2 Drawing Sheets

REVERSIBLE RATCHET DRIVING TOOL

BACKGROUND OF THE INVENTION

1. Field of the Invention

The present invention relates to a hand held, rotary driving tool for enabling rotation of wrenches and other hand tools. The tool comprises a handle giving the user leverage, and a working head which is either directly usable with square drives, screw driving blades, and the like, or which may have a receptacle for interchangeably accepting various tool driving shafts.

2. Description of the Prior Art

Reversible ratcheting tools have long been desired by service and assembly mechanics and technicians for installing and removing threaded fasteners. For the convenience of the technician, it is important that a tool be quickly converted to include any desired driver, blade, socket, and so forth, since efficiency of assembly and disassembly is usually directly linked to the technician's compensation. For this reason, reversible tools have become quite popular.

A second desirable aspect is that a single driving tool enable interchangeable drivers, blades, sockets, and like accessories cooperating with the driver. These tools will be referred to hereinafter as working elements. This enables a single driving tool to perform many tasks. The driving tool can gain added capabilities as additional working elements are made available. This has economic repercussions, since each additional size or configuration requires only a working element of limited complexity and cost.

A number of prior art tools having reversibility and plural driving features will be reviewed. U.S. Pat. No. 3,635,654, issued to Frederick R. McFarland on Jan. 18, 1972, illustrates a two headed driver having reversibly rotating heads. Each head has a socket of different dimensions, so that each head provides two sizes of nut driving sockets. The entire tool will, therefore, provide four total different driving sockets. This tool is limited to the four sizes of sockets originally installed therein. Also, the tool is of complicated construction, requiring a number of internal springs and pawls.

A wrench having a removable socket is shown in U.S. Pat. No. 4,276,791, issued to John W. Thompson on Jul. 7, 1981. The wrench includes the usual bipositionable pawl, and has a lever and linkage for adjusting the driving direction. The present invention is unencumbered by such a pawl and linkage.

Other reversible tools incorporating internal pawls and requiring external manual levers for switching driving direction are seen in U.S. Pat. Nos. 4,807,500, issued to Harvey M. Main on Feb. 28, 1989, 4,819,521, issued to John W. Lang on Apr. 11, 1989, 4,909,106, issued to William E. Foreman on Mar. 20, 1990, and 5,199,332, issued to Ronald W. Batten on Apr. 6, 1993.

Although lacking directional control, the ratchet wrench set forth in U.S. Pat. No. 4,926,720, issued to Kurt Srzanna on May 22, 1990, is of quite complex internal construction, incorporating many small individual parts. The present invention avoids such internal construction.

None of the above inventions and patents, taken either singly or in combination, is seen to describe the instant invention as claimed.

SUMMARY OF THE INVENTION

The present inventive tool combines the advantages of uncomplicated construction with the features of reversibility and interchangeability of tool varieties. The tool has a head containing the operative components, and an elongated handle.

The head has a member which rotates unidirectionally by a ratchet. A receptacle is rotatably disposed within the head. The head has an internal chamber of circular configuration. Part of the circular inner wall of the head is smooth, and part has inwardly oriented teeth. The receptacle has an external wall corresponding to the internal wall of the head. The receptacle wall also has a smooth section and a toothed section. The teeth are pitched in well known fashion to interengage when torque is applied in one direction, and to slip when torque is applied in the opposite direction.

A leaf spring urges the receptacle into the engaged position. The effort of this spring is overcome when the head is rotated in a direction opposite that in which the receptacle and head lock together.

The receptacle has a square hole for receiving insertable tools, such as a screw driver blade, sockets, and the like. A plurality of insertable tools of different dimensional and configurational characteristics gives interchangeability of purpose. The square hole may also drive a square headed fastener directly.

Reversing is accomplished by inverting the tool within the user's hand, so that a similar insertable tool projects towards the workpiece. But having reversed the tool, the direction in which the receptacle slips and locks up is changed. Effort of switching hand position of the tool is approximately the same as engaging and moving an actuating lever by finger, as is commonly performed in prior art tools to change direction.

Accordingly, it is a principal object of the invention to provide a reversing, ratchet action driving tool for driving tools such as screw driver blades and sockets.

It is another object of the invention to allow for interchangeability of individual tool sizes and types.

It is a further object of the invention to eliminate complicated internal construction of the driver.

It is an additional object of the invention to eliminate the requirement for a separate socket for at least one size of fastener head.

It is an object of the invention to provide improved elements and arrangements thereof in an apparatus for the purposes described which is inexpensive, dependable and fully effective in accomplishing its intended purposes.

These and other objects of the present invention will become readily apparent upon further review of the following specification and drawings.

BRIEF DESCRIPTION OF THE DRAWINGS

Similar reference characters denote corresponding features consistently throughout the attached drawings.

DETAILED DESCRIPTION OF THE PREFERRED EMBODIMENTS

Figure 1:
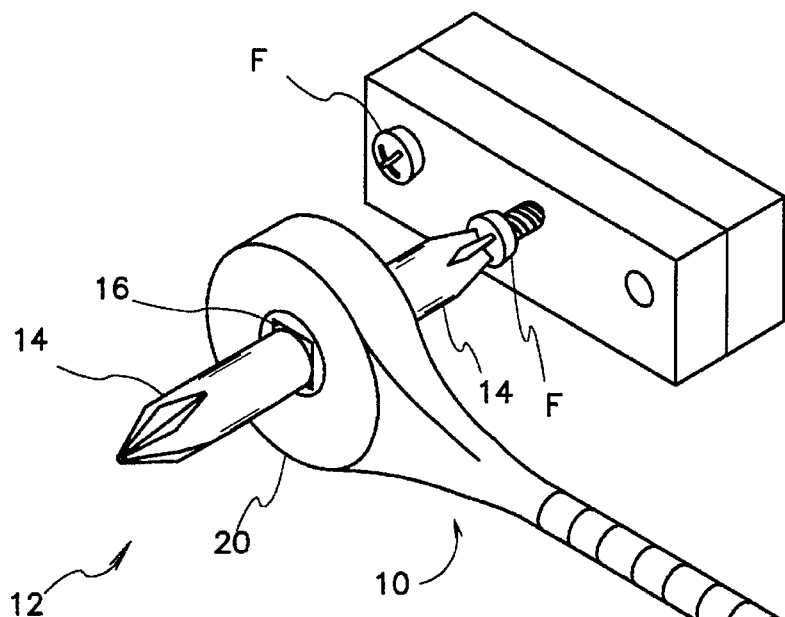
FIG. 1 is an environmental, perspective view of the invention, illustrating one particular type of working dement.

The novel reversible ratchet driving tool 10 is seen in FIG. 1 in combination with one embodiment of a working insert 12. For the purposes of discussion of tool 10, a working insert will be understood to encompass any device which is insertable into or similarly engageable with the basic tool 10, and has structure for engaging tool 10 and two oppositely oriented working elements 14. A working element 14 is a screw driver blade, socket, square drive, hexagonal drive, or any other device for engaging a fastener F or workpiece for the purpose of tightening and loosening the same. In FIG. 1, working elements 14 are seen each to comprise Phillips type screw driver blades attached to a centrally located square block 16.

Block 16 engages an opening (see FIG. 2) formed in tool 10. Block 16 must have a configuration including surfaces which slidingly penetrate the opening, so that working inserts are readily removable and insertable, and therefore, interchangeable. The surfaces of block 16 are also arranged to prevent mutual rotation between working insert 12 and tool 10.

Working elements 14 are preferably similar in dimensions and configuration. This enables immediate reversal of direction when turning fastener F by employing the idle working element 14, and abandoning use of the formerly engaged working element 14. The user need merely rotate tool 10 one hundred eighty degrees about the axis of tool handle 18. However, working elements 14 could vary in dimension or in configuration, if it were desired to increase the types of working elements while minimizing the number of working inserts 12.

Figure 3:
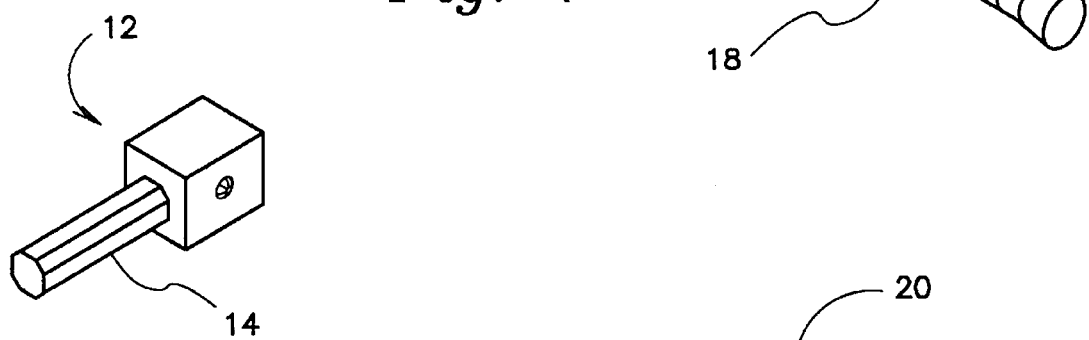
FIG. 3 is a perspective detail view of a different working element.

An example of another configuration of working insert 12 is illustrated in FIG. 3, wherein working element 14 comprises a hexagonal key. In this embodiment, there is no corresponding oppositely oriented working element.

Figure 2:
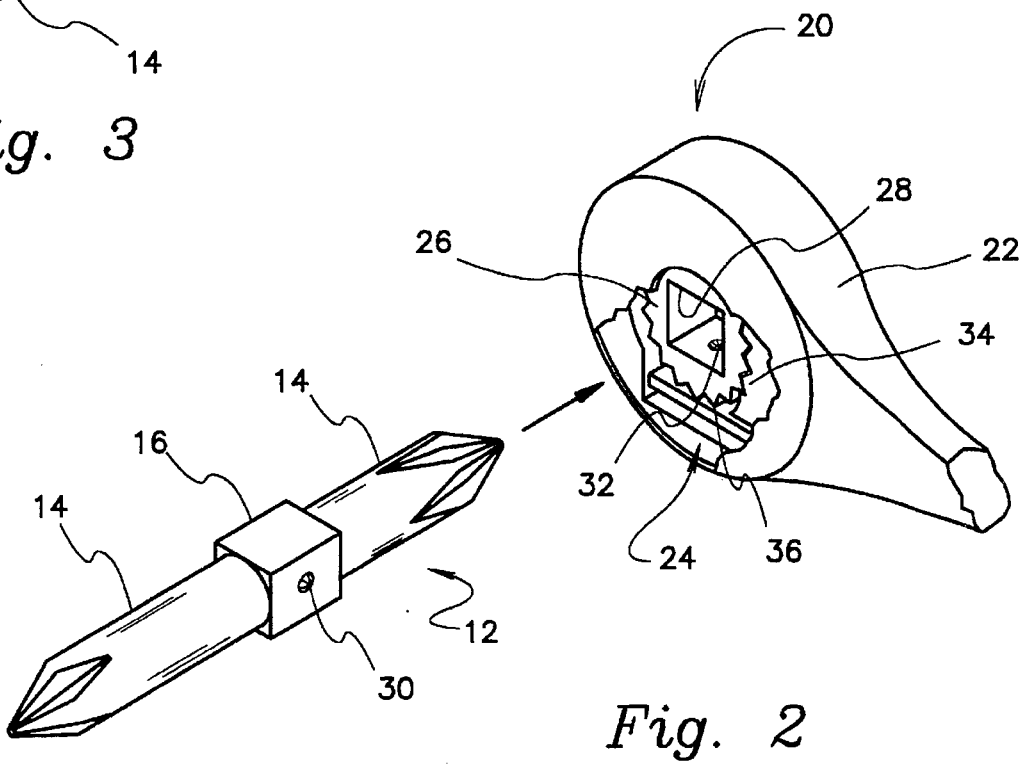
FIG. 2 is an exploded detail view of the novel tool, showing cooperation between the working dement and the head of the tool, and drawn to enlarged scale.

Internal components of working head 20 will now be described, with reference to FIG. 2. Working head 20 forms a housing or thick external wall 22 defining a generally circular chamber 24 therein. A star wheel 26 is rotatably disposed within chamber 24. Star wheel 26 has a square hole or like opening 28 for receiving and engaging block 16 of working insert 12. A square or other non-circular configuration prevents relative rotation between working insert 12 and star wheel 26. Note that the star wheel 26 is prevented from side to side motion by the enclosing lips best seen in the partial cutaway view of FIG. 2.

Engagement of block 16 with opening 28 is enhanced by a spring urged ball 30 located in block 16, which cooperates with a depression 32 formed in one facet of opening 28.

Rotation of star wheel 26 within working head 20 is by ratcheting action. The internal surface of chamber 24 has internally directed teeth 34, and the external surface of star wheel 26 has interfitting, cooperating externally directed teeth 36. Each tooth 34 or 36 is triangular, having two exposed intersecting faces and a base which is undefined by virtue of being integral with wall 22 or with star wheel 26. The exposed intersecting faces are disposed in the usual manner of ratcheting devices, conventional fashion, wherein the faces are each disposed at a pitch causing slippage when tool 10 is rotated or urged in one direction, and causing engagement when tool 10 is rotated or urged in the other direction.

Figure 4:
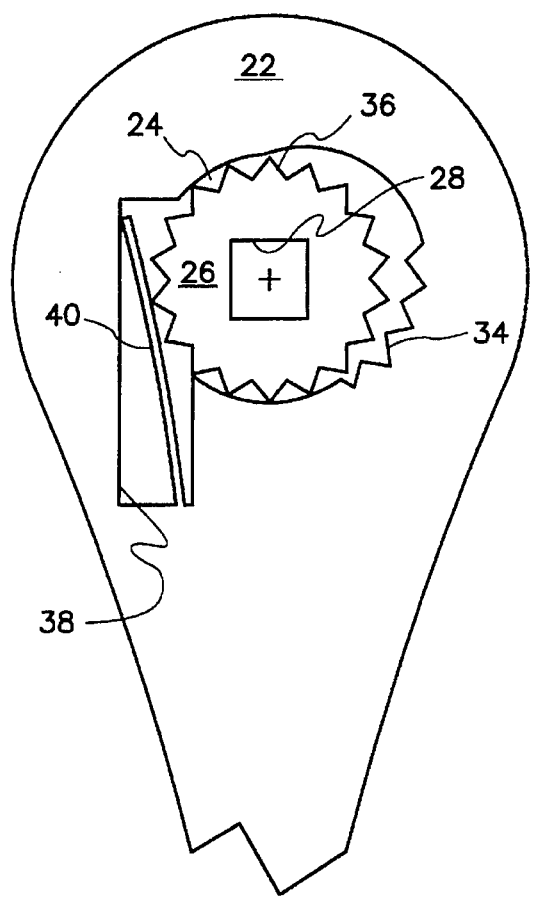
FIG. 4 is a cutaway side view showing slippage ensuing when the tool is rotated in a direction opposite that of the driving direction.

Turning now to FIG. 4, chamber 24 is seen to be generally circular, except for teeth 34 and a connected opening 38 accommodating a leaf spring 40. Spring 40 is anchored to working head 20, occupying opening 38, and normally bears against star wheel 26, urging it into engagement with wall 22.

Figure 5:
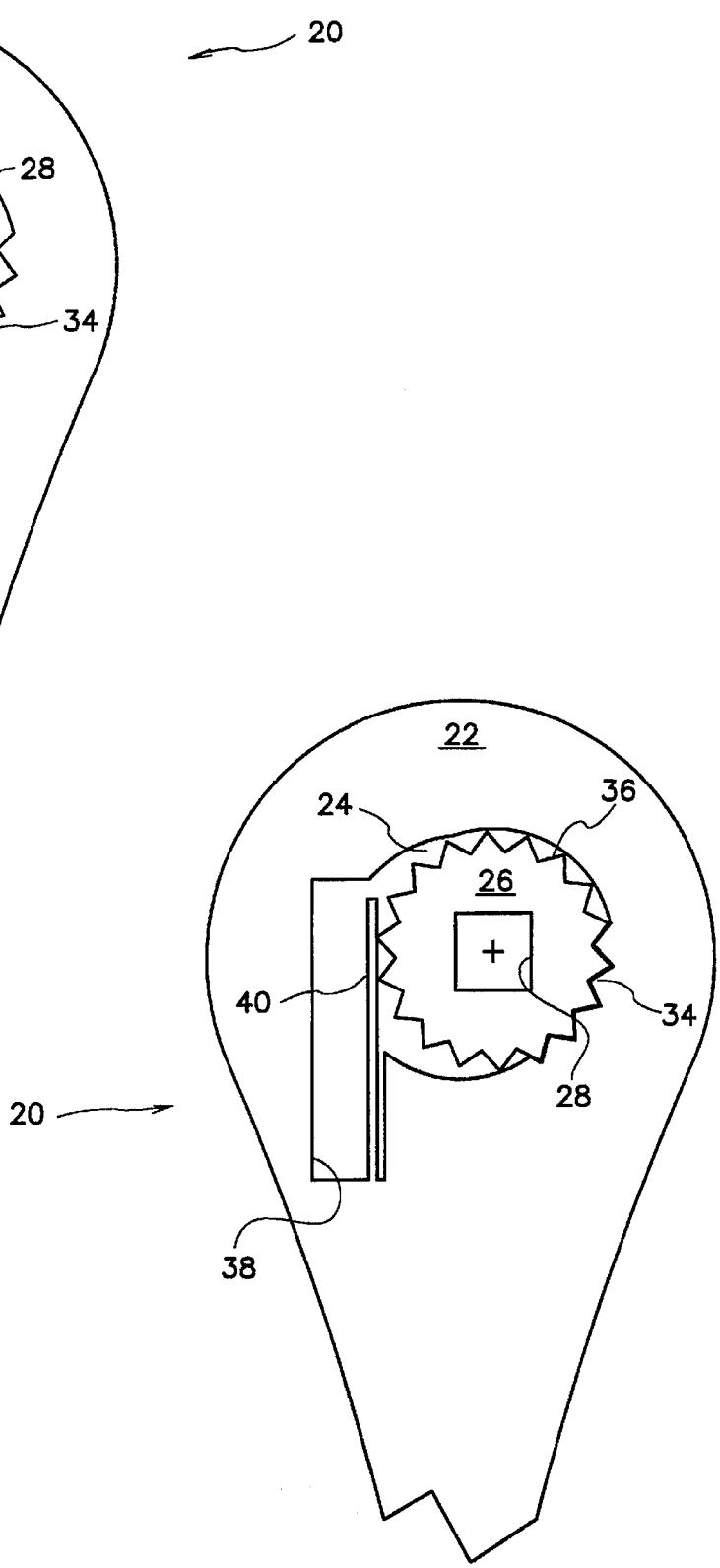
FIG. 5 is a cutaway side view of the working head of the novel wrench, showing the driver in a driven condition.

Star wheel 26 is also generally circular, the peaks and valleys of teeth 36 respectively defining a generally circular perimeter. When engaged with working head 20, as depicted in FIG. 5, star wheel 26 is constrained against rotation within chamber 24. Spring 40 yieldingly prevents disengagement of star wheel 26, remaining straight as depicted.

FIG. 4 shows disengagement of star wheel 26 from wall 20. Under sufficient torque applied in the direction opposite that causing engagement, spring 40 will yield to star wheel 26, deflecting to allow star wheel 26 to move to the center of chamber 24. At this location, teeth 34 and 36 are out of mutual engagement, and star wheel 26 is free to rotate relative to working head 20. When in use, star wheel 26 will remain stationary, a working insert (see FIG. 1) immobilizing star wheel 26 by engagement with a fastener F, and it is working head 20 that will actually rotate.

The geometry of chamber 24 is such that its inner surface has a section bearing teeth 34, the remaining section of this surface being smooth to promote rotation of star wheel 26 when not engaging working head 20.

To summarize, then, spring 40, star wheel 26, and the geometry of chamber 24 combine to immobilize star wheel 26 such that when torque is applied in one direction, star wheel 26 is driven in lockstep with working head 20. When torque is applied in the other direction, star wheel 26 pushes aside spring 40, and disengages from working head 20.

It is preferred that tool 10 be provided with a plurality of working inserts 12 having varying characteristics of dimension and configuration. A set of tools is thereby provided which requires but one driver and interchangeable working inserts to perform many tasks.

It is to be understood that the present invention is not limited to the embodiments described above, but encompasses any and all embodiments within the scope of the following claims.

I claim:

1. A reversible ratchet driving tool having interchangeable working inserts, comprising:

a working head having an elongated handle and having means defining a chamber therein, said chamber having a generally circular internal surface having a first portion including internally directed teeth and a second portion of smooth surface; and a driven receptacle rotatably disposed within said chamber, said receptacle having a circular external surface including externally directed teeth interfittably cooperating with said internally directed teeth of said working head, said receptacle further having means for engaging a working insert usable with said reversible driving tool, said working head further including a spring biasing said receptacle into engagement with said working head by yieldingly urging said externally directed teeth of said receptacle into interfitting engagement of said internally directed teeth of said working head.

2. The reversible ratchet driving tool according to claim 1, wherein each one of said externally directed teeth of said receptacle and said internally directed teeth of said working head is triangular and has two exposed intersecting faces disposed at a pitch causing slippage when said reversible driving tool is rotated in one direction and causing engagement when said reversible driving tool is rotated in the other direction.

3. The reversible ratchet driving tool according to claim 1, wherein said spring is a leaf spring anchored to said working head within said chamber and contacting said driven receptacle, and yieldably urging said driven receptacle radially into engagement with said internally directed teeth of said working head, whereby torque applied in one direction rotates said driven receptacle in lockstep with said working head, and torque applied in the other direction causes said driven receptacle to push aside said spring and disengage from said working head.

4. The reversible ratchet driving tool according to claim 1, said means for engaging a working insert further
    defining an opening formed in said driven receptacle, for receiving a working insert insertable thereinto, and
    including means for preventing relative rotation of the working insert and said driven receptacle.

5. The reversible ratchet driving tool according to claim 4, said opening formed in said driven receptacle being a square hole.

6. The reversible ratchet driving tool according to claim 1, further including a working insert having
    a central external surface for engaging said opening formed in said driven receptacle, and
    oppositely oriented working elements.

7. The reversible ratchet driving tool according to claim 6, wherein said oppositely oriented working elements are similar elements.

8. The reversible ratchet driving tool according to claim 6, further comprising a plurality of working inserts of varying characteristics, whereby many tasks may be performed by interchanging said working inserts inserted into said reversible driving tool.

9. A reversible ratchet driving tool having interchangeable working inserts, comprising:
    a working head having an elongated handle and having means defining a chamber therein, said chamber having a generally circular internal surface having a first portion including internally directed teeth and a second portion of smooth surface; and
    a driven receptacle rotatably disposed within said chamber, said receptacle having a circular external surface including externally directed teeth interfittably cooperating with said internally directed teeth of said working head, said receptacle further having means defining an opening formed in said driven receptacle, for receiving a working insert insertable thereinto, and means for preventing relative rotation of the working insert and said driven receptacle, said working head further including a spring biasing said receptacle into engagement with said working head by yieldingly urging said externally directed teeth of said receptacle into interfitting engagement of said internally directed teeth of said working head, each one of said externally directed teeth of said receptacle and said internally directed teeth of said working head being triangular and having two exposed intersecting faces disposed at a pitch causing slippage when said reversible driving tool is rotated in one direction and causing engagement when said reversible driving tool is rotated in the other direction.

10. The reversible ratchet driving tool according to claim 9, wherein said spring is a leaf spring anchored to said working head within said chamber and contacting said driven receptacle, and yieldably urging said driven receptacle radially into engagement with said internally directed teeth of said working head, whereby torque applied in one direction rotates said driven receptacle in lockstep with said working head, and torque applied in the other direction causes said driven receptacle to push aside said spring and disengage from said working head.

11. The reversible ratchet driving tool according to claim 9, said opening formed in said driven receptacle being a square hole.

12. The reversible ratchet driving tool according to claim 9, further including a working insert having
    a central external surface for engaging said opening formed in said driven receptacle, and
    oppositely oriented working elements.

13. The reversible ratchet driving tool according to claim 12, wherein said oppositely oriented working elements are similar elements.

14. The reversible ratchet driving tool according to claim 12, further comprising a plurality of working inserts of varying characteristics, whereby many tasks may be performed by interchanging said working inserts inserted into said reversible driving tool.

15. A reversible ratchet driving tool having interchangeable working inserts, comprising:
    a working head having a handle and having means defining a chamber therein, said chamber having an internal surface having a first portion including internally directed teeth and a second portion of smooth surface; and
    a driven receptacle rotatably disposed within said chamber, said receptacle having a circular external surface including externally directed teeth interfittably cooperating with said internally directed teeth of said working head, said receptacle further having means for engaging a working insert usable with said reversible driving tool, said working head further including resilient bias means for biasing said receptacle into engagement with said working head by urging said externally directed teeth of said receptacle into interfitting engagement of said internally directed teeth of said working head when said handle is forced in a first direction and out of engagement with said working head by urging said externally directed teeth of said receptacle away from interfitting engagement of said internally directed teeth of said working head when said handle is forced in a second direction.

16. The reversible ratchet driving tool according to claim 15, wherein said resilient bias means is a spring normally urging said externally directed teeth of said receptacle into interfitting engagement of said internally directed teeth of said working head.

* * * * *